United States Patent [19]

Mann et al.

[11] Patent Number: 5,423,972
[45] Date of Patent: Jun. 13, 1995

[54] WATERTIGHT EXHAUST GAS SENSOR

[75] Inventors: Gamdur S. Mann, Grand Blanc; Charles D. Oakley, Lapeer, both of Mich.

[73] Assignee: General Motors Corporation, Detroit, Mich.

[21] Appl. No.: 181,946

[22] Filed: Jan. 18, 1994

[51] Int. Cl.⁶ .............. G01N 27/409; G01N 27/417
[52] U.S. Cl. ........................ 204/424; 204/427; 204/428
[58] Field of Search .............. 204/153.18, 421–429

[56] References Cited

U.S. PATENT DOCUMENTS

| | | | |
|---|---|---|---|
| 4,212,720 | 7/1980 | Maurer et al. | 204/428 |
| 4,219,399 | 8/1980 | Gruner et al. | 204/428 |
| 4,526,672 | 7/1985 | Reed | 204/428 |
| 4,556,475 | 12/1985 | Bayha et al. | 204/427 |
| 4,597,849 | 7/1986 | Burkhardt et al. | 204/424 |
| 4,786,397 | 11/1988 | Barbieri et al. | 204/427 |
| 4,818,363 | 4/1989 | Bayha et al. | 204/426 |
| 4,818,364 | 4/1989 | Weber et al. | 204/427 |
| 5,246,562 | 9/1993 | Weyl et al. | 204/424 |

Primary Examiner—T. Tung
Attorney, Agent, or Firm—Cary W. Brooks

[57] ABSTRACT

The invention includes an automotive exhaust gas sensor including an inside belleville design, wherein a belleville spring is located inside a middle shell sub-assembly and below an upper insulator. The design provides for improved interior loading pressures with improved resiliency for a self-contained air reference source exhaust gas sensors.

2 Claims, 3 Drawing Sheets

WATERTIGHT EXHAUST GAS SENSOR

FIELD OF THE INVENTION

This invention relates to gas sensors, and more particularly, to automotive exhaust gas sensors with an internal assembly belleville washer.

BACKGROUND OF THE INVENTION

A variety of automotive exhaust gas sensors are known. FIG. 1 illustrates a prior art sealed, watertight oxygen gas sensor 10 including electrical leads 12, 14, 16 connecting to a heating element 18, and to internal and external electrodes 20, 22 surrounding a conical-shaped electrolyte body 24 made of zirconia. The exhaust sensor housing includes a lower tubular louvered shell 26, a thicker middle shell 28 and an upper tubular shell 30. The conical-shaped electrolyte body and heater are held in position by a sub-assembly including an upper ceramic insulator through which a heating element passes. An annular finger 32 of the middle shell is crimped over a first shoulder 34 formed in the upper ceramic insulator to hold the electrolyte body and heater in position. A belleville washer 36 is positioned above the middle housing and located to be biased against a shoulder 38 formed in the upper tubular shell and a second shoulder 35 formed on the upper ceramic insulator body. During the operation of the oxygen sensor, the assembly undergoes thermal expansion and contraction. The belleville washer is positioned to provide a downward force on the upper ceramic insulator body and thus the heating element 18 and electrolyte body 24 to maintain their position and electrical contact within the sensor. The downward force of the belleville washer also maintains a tight seal by way of a lower annular gasket 37 positioned between a lower sloped shoulder 39 of the electrolyte body and a sloped shoulder 41 of the middle shell to provide a gastight seal.

However, this design illustrated in FIG. 1 is not optimal. When the annular finger 32 of the middle shell is crimped over the first shoulder 34 of the upper ceramic insulator, the crimped finger can bind the ceramic insulator so that the insulator moves with the expansion of the middle shell. However, since the ceramic insulator is stuck in the middle shell, the belleville washer 36 cannot transmit a sufficient force to maintain a seal on the lower gasket 37 between the lower sloped shoulder 39 of the electrolyte body and the lower sloped shoulder 41 of the middle shell. Thus, this design can result in exhaust gas entering the housing and contaminating the air reference gas for the sensing device. The exhaust gas entering through the lower seal results in displacement of reference oxygen and can result in a lower oxygen concentration on the wrong side (the side of the inner electrolyte body wall forming the conical-shaped cavity) of the electrolyte body thus resulting in a negative signal shift being produced by the oxygen sensor.

FIG. 2 illustrates a water resistant design in which the upper shell 50 is not hermetically welded to the middle shell 52, but is mechanically secured with a locking washer 54 located above a crimp finger 56 of the middle shell. The upper shell 50 is pushed downward over the locking washer. The locking washer 54 provides a friction fit and bends downward as the upper shell 50 is pushed down, but digs into the upper shell 50 when it is lifted upward. This type of sensor has a air reference that is open to the atmosphere. This design is much less sensitive to exhaust gas leakage into the air reference side of the sensing element because of the dilution of leaking exhaust gas by the atmosphere. This design utilizes a wave washer disk spring (shown in FIG. 3) 58 in the internal assembly. The assembly includes an upper ceramic insulator 60 having a upper sloped shoulder 59 and a flat lower shoulder 61. A hole is formed in the upper ceramic insulator for receiving a heating element 18. A terminal post 62 for the heating element extends through the electrolyte body and includes an outwardly extending annular flat 72. A gripper 63 is carried inside the terminal post. The conical-shaped electrolyte body 64 is surrounded by inner and outer electrodes 66, 68. The conical-shaped electrolyte body includes a lower sloped shoulder 76 which engages an annular lower gasket 70 resting on a lower sloped shoulder 78 of the middle shell. An open nipple of an upper gasket 74 extends into the open end of the conical-shaped electrolyte body and also includes an annular flat which rests against an upper shoulder of the electrolyte body. A wave washer spring 58 is positioned between an upper ceramic insulator 60 and the terminal post 62. An annular finger 56 of the middle shell is crimped over the upper ceramic insulator 60. The vented air reference chamber provides the sensor with a continuous source of reference oxygen and therefore this type of sensor is less sensitive to the problems associated with "watertight" oxygen sensors having internal exhaust leaks. Further, application of wave-type washers have shown limited resiliency and are only capable of exerting a load of about 200-300 lbs.

Thus, heretofore, there has been a need for a watertight, sealed automotive exhaust gas sensor which overcomes the deficiencies of the prior art.

SUMMARY OF THE INVENTION

The invention includes an automotive exhaust gas sensor including an inside belleville design, wherein a belleville spring is located inside a middle shell sub-assembly and below an upper insulator. The design provides for improved loading pressures with improved resiliency for a self-contained air reference source exhaust gas sensors.

These and other objects, features and advantages of the present invention will become more apparent from the following brief description of the drawings, detailed description, and appended claims and drawings.

DETAILED DESCRIPTION

Figures 4, 5:
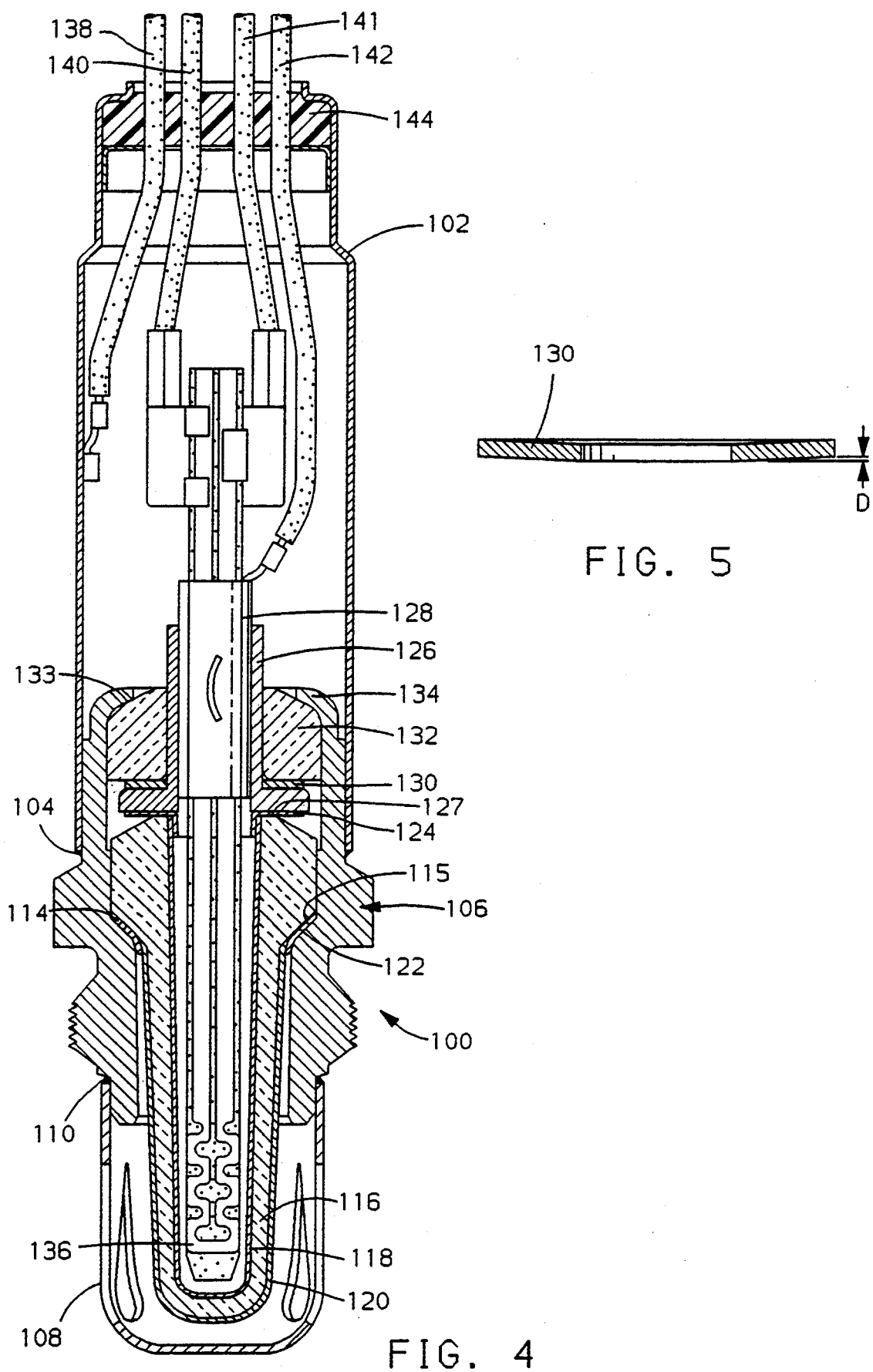
FIG. 4 illustrates a watertight exhaust gas sensor including a belleville washer located inside the middle shell sub-assembly according to the present invention.
FIG. 5 illustrates a belleville washer utilized in the exhaust sensor illustrated in FIG. 4.

FIG. 4 illustrates an automotive exhaust gas sensor 100 according to the present invention. The sensor includes an upper tubular shell 102 having a lower end laser welded 104 to a thicker middle shell 106. A lower louvered tubular shell 108 is provided having an upper end laser welded 110 to the middle shell as well. The middle shell includes a lower annular shoulder 115 which carries thereon an annular lower gasket 114. A sensing element is carried in the middle shell. The sensing element includes a conical-shaped electrolyte body 116 having inner and outer electrodes 118, 120 formed thereon. The electrolyte body has a lower sloped annular shoulder 122 and the middle shell has a matching sloped shoulder 115. The lower gasket 114 is positioned between shoulders 122 and 115. A nipple-shaped intermediate gasket 124 is provided having an open end extending into the open end of the conical-shaped electrolyte body. The intermediate gasket 124 also includes an outwardly extending annular flat which rests on an upper shoulder 127 of the electrolyte body.

A terminal post 126 is provided including a tubular hollow portion and an outwardly extending annular flat which rests on the flats of the intermediate gasket 124. A gripper 128 is received in the terminal post. A belleville washer 130 having a hole formed therein is slipped over the tubular portion of the terminal post to engage the annular flat of the terminal post. The belleville washer may be made from a suitable high temperature metal such as Inconel 718. The belleville washer has a lower engagement point from which an annular flat is pivoted upwardly to form a concave-shaped washer. A suitable washer has a material thickness of approximately 0.039 inches thick and is constructed so that the vertical distance (D) between the lower engagement point and the upper outer edge of the washer is 0.006 to 0.010 inches. An upper insulator 132 is provided having a hole formed therein which is slipped over the tubular portion of the terminal post. The upper insulator includes a lower shoulder which rests on the belleville washer.

The middle shell includes an annular finger 134 which is crimped over an upper slanted shoulder 133 of the insulator to hold the sub-assembly in place and to apply pressure to the lower gasket. A heating element 136 extends through the terminal post and into the cavity of the conical-shaped electrolyte body.

Four separate wires 138, 140, 141, 142 are provided through the upper shell to make connection to the upper shell as a sensor ground, to the heating element, and to the terminal post to provide connection to the inner electrode of the sensing element. The outer electrode is tied to ground through the electrical connection made to the upper shell through the middle shell and through the lower gasket to the outer electrode. A high temperature polymer seal 144 is provided in the upper portion of the upper shell through which the electrical wires pass which is sufficient to provide a water tight oxygen reference chamber in the upper shield.

Figure 1:
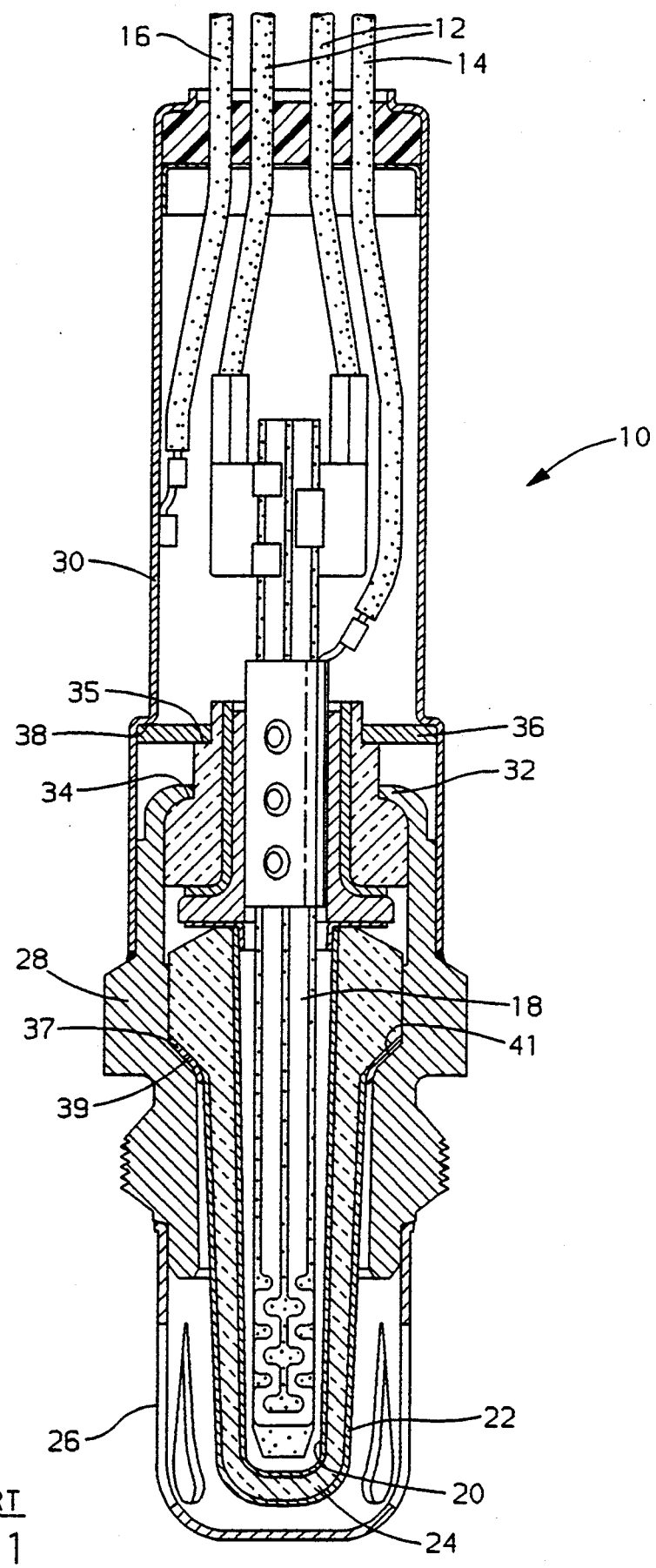
FIG. 1 illustrates a prior art automotive exhaust oxygen sensor including a belleville washer located above the middle shell sub-assembly.
Figure 2:
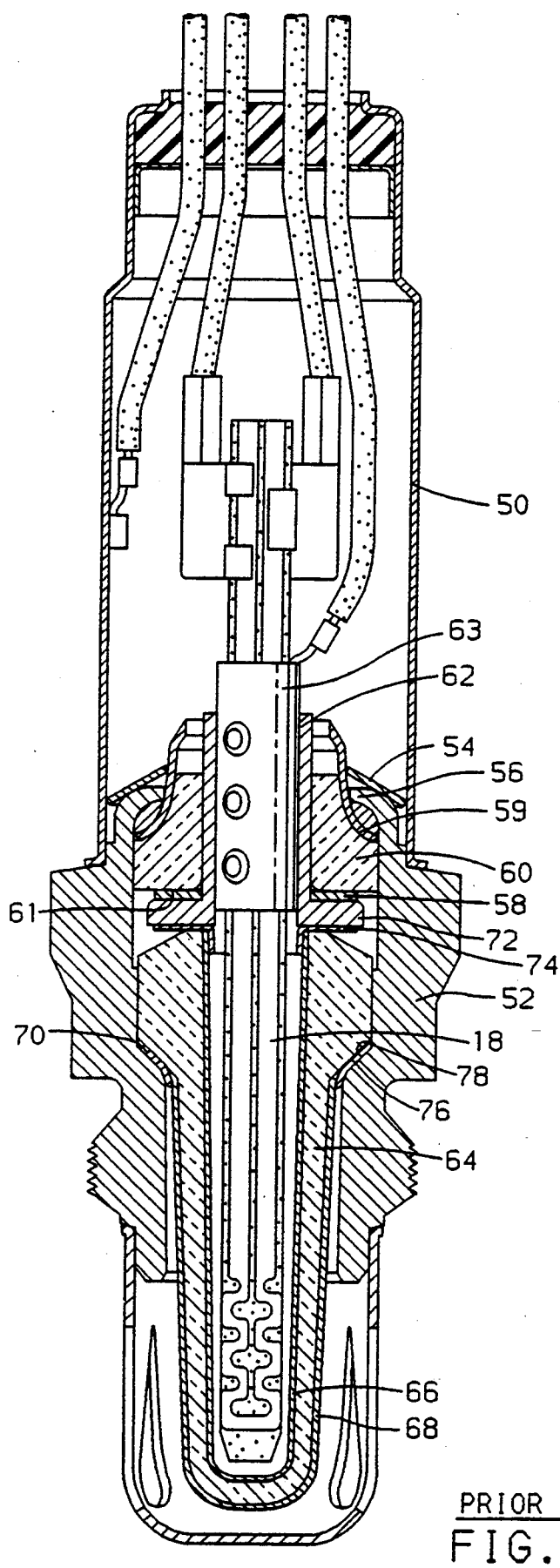
FIG. 2 illustrates a prior art open air reference exhaust oxygen sensor utilizing a wave-washer in the middle shell sub-assembly.
Figure 3:
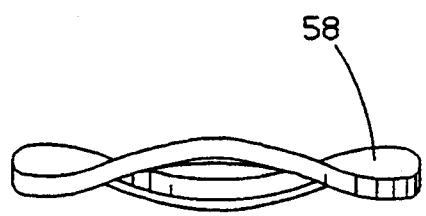
FIG. 3 illustrates a wave-washer according to the prior art.

The use of the belleville washer provides for a resiliency of 6–8/1000th inch capable of loads of 400–500 lbs. to insure an electrical connection. The belleville washer provides an adequate load on the lower gasket 114 to prevent exhaust gas from contaminating the reference air ($O_2$) in the chamber defined by the upper shell during thermal expansion and contraction of sensor components. The use of a belleville washer inside the assembly has further advantages. Often, when the annular finger of the middle shell is crimped over the upper ceramic insulator, the crimping process may result in an unequal load distribution on the lower gasket. Unlike the design illustrated in FIG. 1, using the belleville washer inside the sub-assembly allows for the same load distribution to be exerted on the lower washer during thermal expansion and contraction even when the crimping process results in an uneven load on the lower gasket. In a watertight oxygen sensor design, the cavity provided by the upper tubular shell supplies sufficient reference oxygen to operate the sensor without significant oxygen from an external source. Watertight oxygen sensors are desirable because of underbody installation locations that are exposed to significant road splash during operation.

The embodiments of the invention in which an exclusive property or privilege is claimed are defined as follows:

1. An exhaust gas sensor comprising:
   a watertight upper tubular shell having a lower end welded to a middle shell,
   the middle shell carrying a sensing element seated on a lower annular gasket carried on an inner annular sloped shoulder of the middle shell,
   the sensing element comprising a conical-shaped electrolyte body having an inner electrode and an outer electrode formed thereon,
   an insulator having an upper shoulder,
   a belleville washer disposed between the insulator and the sensing element, said belleville washer having a bottom face providing a lower engagement point from which an annular flat is pivoted upwardly to form a concave-shaped washer and so that the vertical distance between the lower engagement point and an upper outer edge of the bottom face of the washer ranges from about 0.006 to about 0.01 inch,
   wherein said middle shell has a finger crimped over the upper shoulder of the insulator.

2. An exhaust gas sensor as set forth in claim 1 further comprising a lower louvered tubular shell having an upper end connected to the middle shell.

* * * * *